Figure 3A:
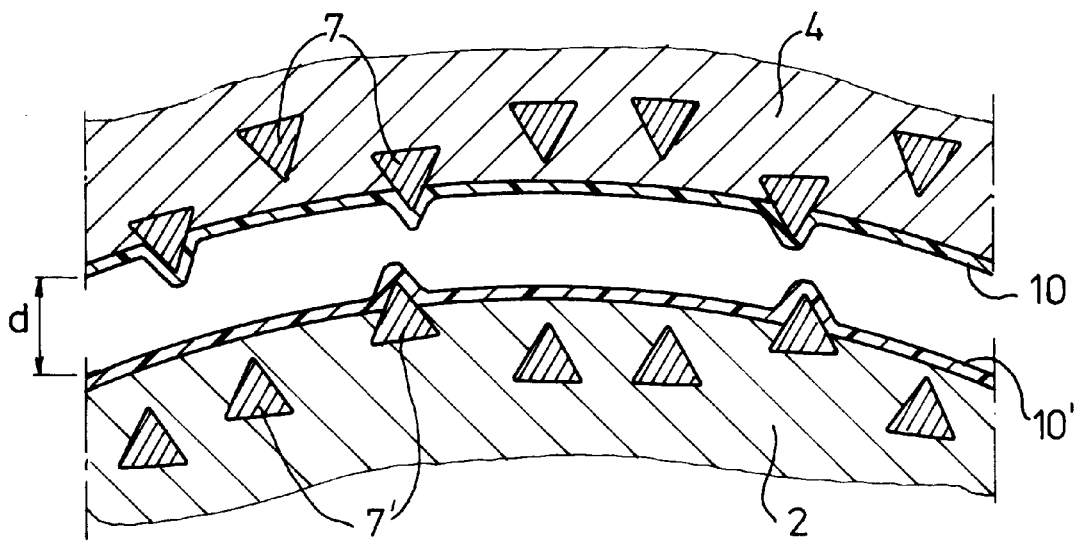

United States Patent
Hamelijnck et al.

[11] Patent Number: 6,120,545
[45] Date of Patent: Sep. 19, 2000

[54] JOINT PROSTHESIS HAVING CERAMIC ABRASION LAYER

[75] Inventors: Karel Hamelijnck, Amsterdam; Roelandt Gustaaf Woering, Baarn, both of Netherlands

[73] Assignees: Accis BV; Johan A. J. van Doorn; Jaap van Straten, all of Netherlands

[21] Appl. No.: 09/269,873

[22] PCT Filed: Oct. 6, 1997

[86] PCT No.: PCT/NL97/00553

§ 371 Date: Apr. 1, 1999

§ 102(e) Date: Apr. 1, 1999

[87] PCT Pub. No.: WO98/14140

PCT Pub. Date: Apr. 9, 1998

[30] Foreign Application Priority Data

Oct. 4, 1996 [NL] Netherlands ............................ 1004207

[51] Int. Cl.[7] .................................................. A61F 2/32
[52] U.S. Cl. ..................................... 623/22.15; 623/18.11
[58] Field of Search ................................ 623/18, 22, 23, 623/18.11, 22.15

[56] References Cited

U.S. PATENT DOCUMENTS 5,365,359  11/1994  Raab .......................................... 3/1.912
5,702,448  12/1997  Buechel et al. ............................ 623/16

FOREIGN PATENT DOCUMENTS

| 0555033 | 8/1993 | European Pat. Off. . |
| 0607017 | 7/1994 | European Pat. Off. . |
| 2088764 | 1/1972 | France . |
| 2636836 | 3/1990 | France . |
| 2327758 | 5/1997 | France . |
| 3211210 | 10/1983 | Germany . |
| 3403589 | 8/1985 | Germany . |
| 3928845 | 3/1991 | Germany . |

*Primary Examiner*—Jeffrey A. Smith

[57] ABSTRACT

The invention relates to a joint prosthesis comprising two metal parts which are movable with respect to one another. The surfaces of the metal parts are covered with an abrasion layer of ceramic material which has a hardness which is greater than that of the carbides present in the metal. The carbides are worn away by the abrasion layer. As a result, the overall wear behavior of the two metal parts of the prosthesis is improved considerably, and the metal surface of the prosthesis parts is not affected by the carbides during movement. The metal components are preferably spaced apart from one another at a distance of at most 0.2 millimeter. This close fit improves the wear action. Owing to the relatively thin wear layer, the particles formed during the wearing process are small enough to be discharged into the space between the joint parts by synovial fluid.

15 Claims, 4 Drawing Sheets

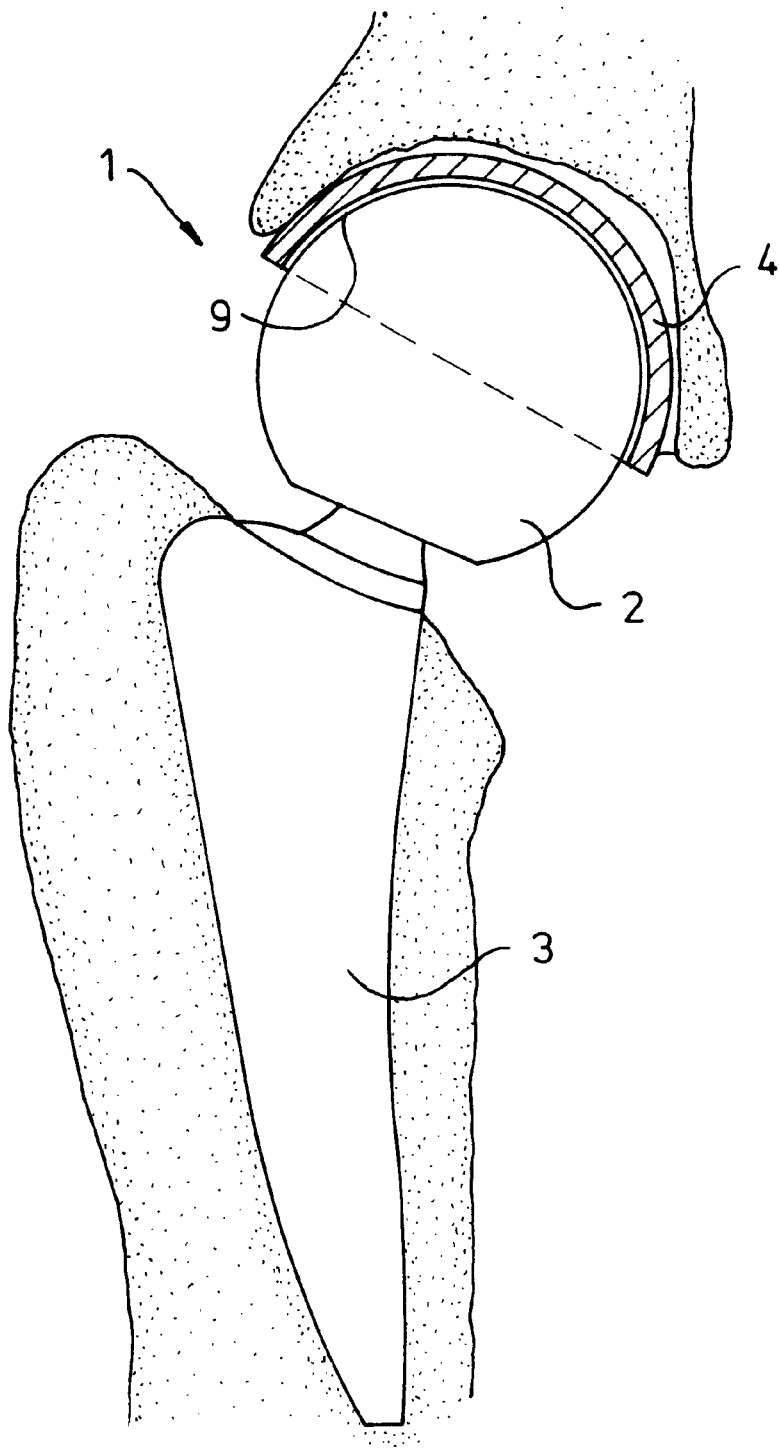

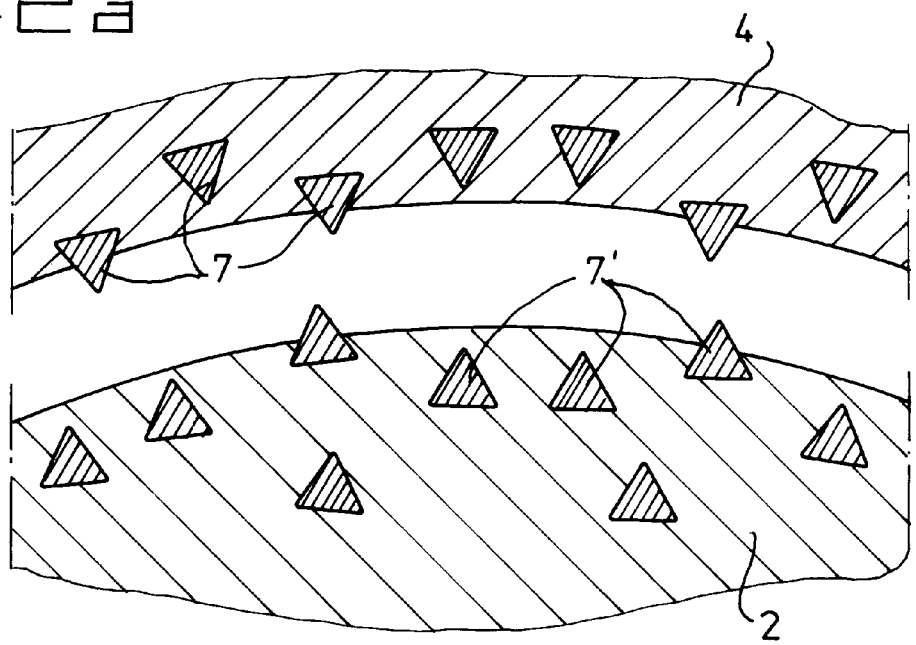
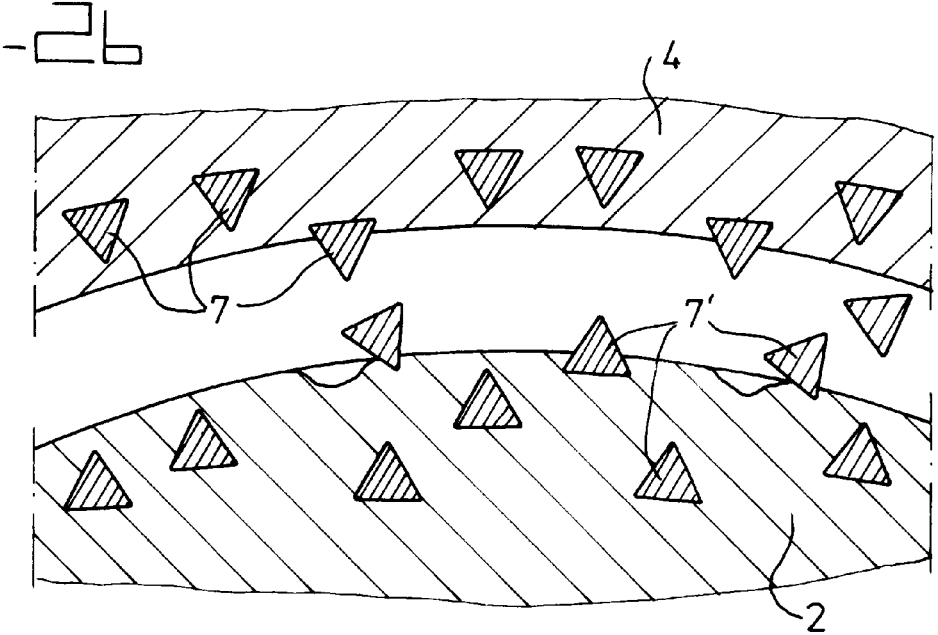

JOINT PROSTHESIS HAVING CERAMIC ABRASION LAYER

The invention relates to a joint prosthesis comprising two metal parts which are movable with respect to one another, the metal parts being coated with a ceramic surface layer.

In known joint prostheses, for example hip prostheses, a spherical head with a diameter of, for example, 28 millimeters is attached to the thighbone. This head may be formed, for example, of CrCoMo or CrCoTi. The hip-joint socket which is attached to the pelvis and in which the head is held rotatably is produced from ultra-high molecular weight polyethylene.

It is also known to form femoral heads from ceramic material, such as aluminium oxide. The disadvantage of using polyethylene in the hip-joint socket is that the polyethylene is worn down by the surface of the head rubbing along the socket. This wear may amount to 100 to 200 microns per annum. This results in the formation of polyethylene particles which accumulate in the tissue cells in the vicinity of the prosthesis and which may cause a reaction, which might lead to the stem of the femoral head giving way.

The problem caused by the formation of polyethylene particles as a result of wear can be avoided by the use of a metal hip-joint socket and femoral head. In this case, both the head and the socket may be formed, for example, from chromium cobalt molybdenum alloys. The disadvantage of metal-on-metal prostheses is that during the casting process compounds are formed with carbon, i.e. the so-called carbides. In the case of the chromium cobalt molybdenum prostheses, these are so-called M7C3 carbides. The dimensions of these compounds is between 20 and 30 micrometers. The carbides may project above the surface of the head and the socket and, after being worn away, may pass into the joint cavity between the moving parts of the prosthesis. Improved casting methods and accurate surface treatments have allowed the dimensions of the carbides to be limited to 3–10 micrometers.

From FR-A-2088764 a hip protheses is known comprising a head and hip-joint socket which are coated with a wear resistant material, according to the preamble of claim 1. The wear resistant material is contacted with the surfaces at supersonic velocities. The head and socket may be comprised of a CrCoMo alloy, the wear resistant material being a ceramic material. When the ceramic material wears away upon use, undesired metal to metal contact or contact of metal on ceramic material may cause release of metal or ceramic particles into the gap of the prostheses.

It is an object of the present invention to provide a joint prosthesis in which wear is counteracted in an effective manner and which is compatible with the human body without causing reactions. It is a further object of the present invention to provide a joint prosthesis which has a long useful service life.

To this end, the joint prosthesis according to the invention is characterized in that the surfaces are covered with an abrasion layer of ceramic material which has a hardness greater than that of the carbides, the thickness of the abrasion layer being less than 0.5 micrometer, preferably virtually equal to 0.3 micrometer. It has been found that, by applying an abrasion layer made of ceramic material which is harder than the carbides, these carbides can be worn away by the abrasion layer. Since the ceramic layer is relatively thin, the particles which are formed during the wear process of the carbides are smaller than 0.1 micrometer. The particles which are formed by the wear process and have such a dimension can be discharged by the synovial fluid which is present between the movable parts of the prosthesis and removed via the lymphatic system. As a result, these released particles do not contribute further to wear to the parts of the prosthesis.

The metal parts of the prosthesis are preferably spaced apart from one another at a distance of at most 0.4 millimeter, preferably at most 0.2 millimeter. This small degree of play between the two movable components results in a low frictional resistance and leads to optimum initial wearing-away of the carbides. An advantageous material for the ceramic abrasion layer is formed by TiNbON, i.e. titanium niobium oxide nitrite. This material is harder than the M7C3 carbides formed in CrCoMo, with a relative hardness of $35313 \pm 2994$ N/mm$^2$, compared to a carbide hardness of $17083 \pm 776$ N/mm$^2$ and a hardness of the CrCoMo of $7869 \pm 321$ N/mm$^2$.

In one embodiment according to the invention, the joint prosthesis comprises a femoral head and hip-joint socket in which the diameter of the head is at least 40 mm. Using a relatively large diameter of the head reduces the effect of unevenness on the wear and frictional properties and creates as large a contact area as possible. As a result, minimum wear takes place owing to a better distribution of the loading force.

Figure 3B:
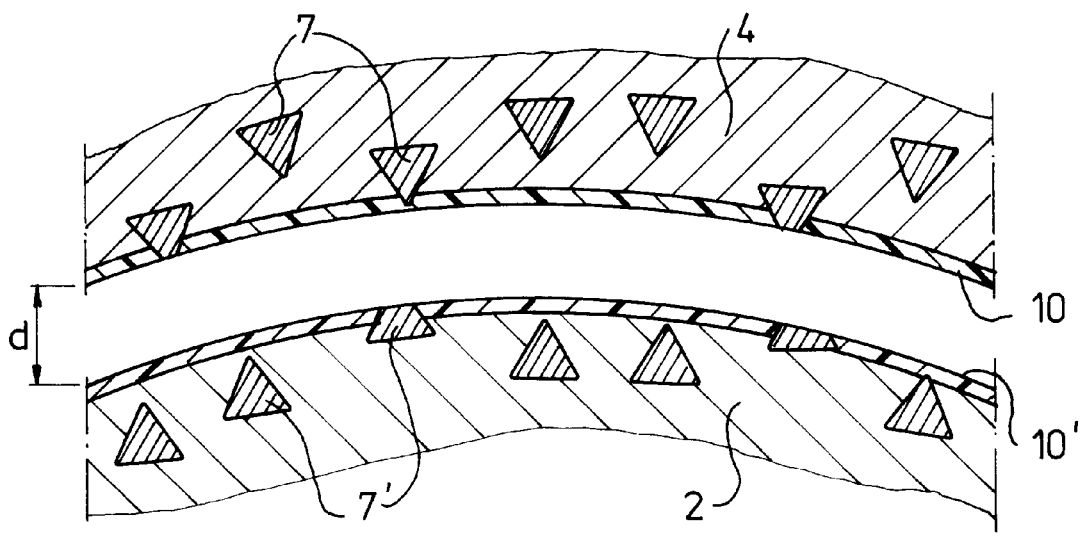
Figure 4:
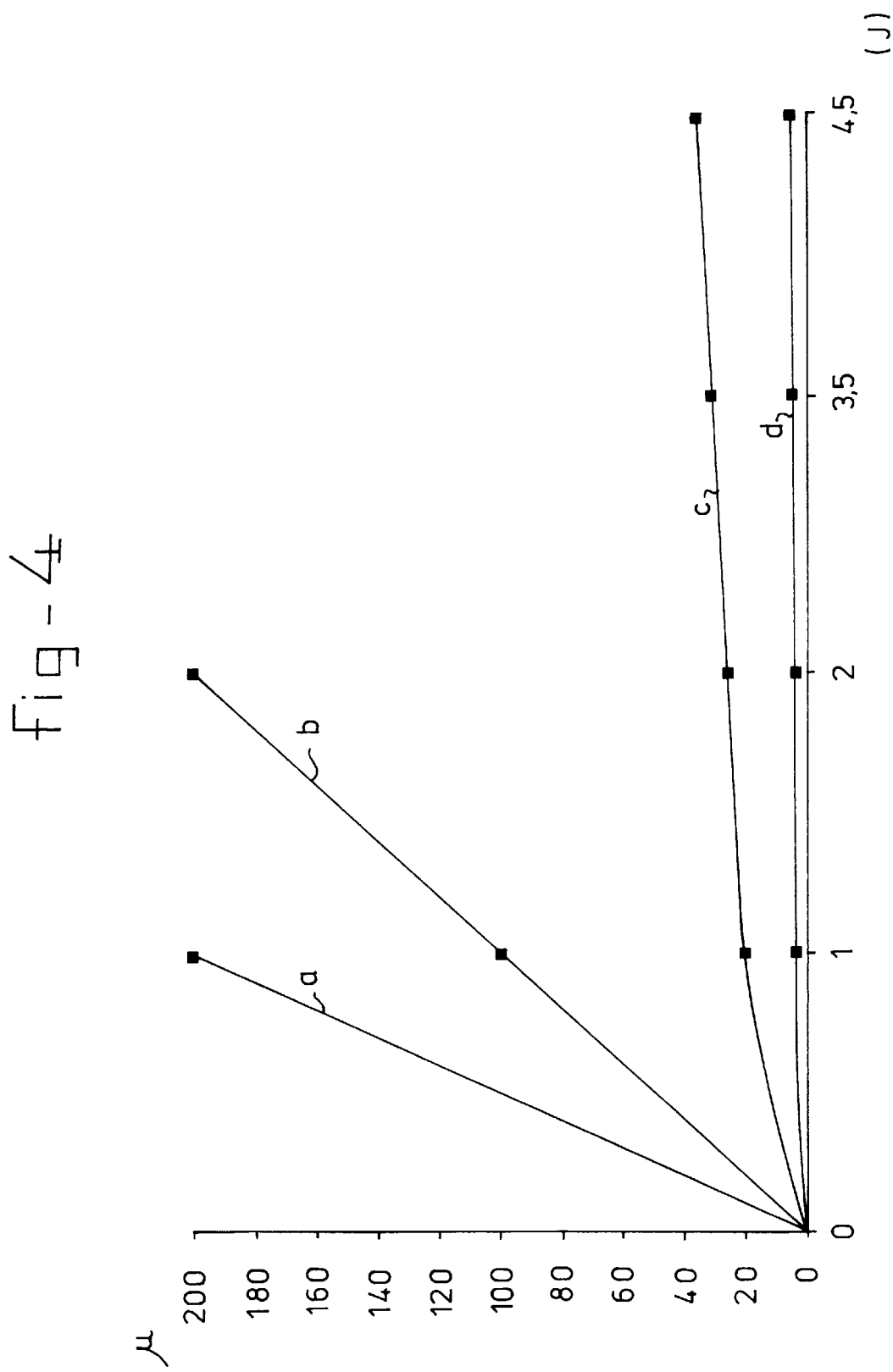

An embodiment of a joint prosthesis according to the present invention will be explained in more detail with reference to the attached drawing, in which:

FIG. 1 shows a diagrammatic side view of a femoral head and a hip-joint socket,

FIGS. 2a and 2b diagrammatically show a structure of the surfaces of a femoral head and hip-joint socket without a TiNbON coating, FIGS. 3a and 3b diagrammatically show the structure of the surfaces of the head with an abrasion layer or coating, and FIG. 4 shows a graph depicting the wear to various materials of a femoral head and hip-joint socket.

FIG. 1 shows a diagrammatic side view of a joint prosthesis 1 in the form of a femoral head 2 and a socket 4. The head 2 is anchored in the hipbone by a stem 3. A joint cavity 9 which has a width of about 0.2 millimeter is situated between the socket 4 and the head 2. The head 2 according to the invention and the socket 4 are formed from a metal alloy, such as for example CrCoMo, i.e. chromium cobalt molybdenum. As shown in FIGS. 2a and 2b, carbides 7, 7' project from the surface of both the head 2 and the socket 4.

These carbides are formed during the casting process and can move to above the surface when the head and the socket are subject to load. The carbides may cause wear in the CrCoMo, or may break off, as shown in FIG. 2b, thus causing "third body wear". According to the invention, an abrasion or wear layer 10, 10' made of a ceramic material, such as TiNbON, with a greater hardness than that of the carbides 7, 7', is applied over the carbides 7, 7'. This is shown in FIGS. 3a and 3b. When the head 2 moves in the socket 4, the carbides 7, 7', projecting above the wear layer 10, of a surface 4, 2 will wear away against the opposite surface. Since the distance d, between the socket 4 and the head 2 is relatively small, amounting to approximately 0.2 millimeter, this close fit means that the carbides 7, 7' are worn away. During the wear-down phase, the ceramic layers 10, 10' first of all have a polishing effect on one another. At the places where the TiNbON layer 10, 10' has worn away completely, a homogeneous substrate is formed. The size of the particles worn away is less than 0.1 micrometer, so that these particles are removed from the space between the head 2 and the socket 4 by the synovial fluid present in the cavity 9.

FIG. 4 shows a graph of the wear of a femoral head and hip-joint socket made of various materials. To gain this information, a joint simulator was used to move a femoral head in a hip-joint socket. The wear in microns is plotted on the vertical axis, and the number of movement cycles is plotted on the horizontal axis, one year corresponding to $10^6$ relative movements.

Plot a shows the wear curve for a femoral head made of metal and with a diameter of 22 mm and a hip-joint socket made of ultra-high molecular weight polyethylene.

Plot b shows the curve for wear between a ceramic femoral head of 28 mm and a hip-joint socket made of polyethylene. Plot c shows the curve for wear between a femoral head made of CrCoMo with a diameter of 37 mm and a hip-joint socket which is likewise made of CrCoMo.

Plot d shows the wear curve of a femoral head and a hip-joint socket according to the invention made of CrCoMo covered with a wear layer which is made of TiNbON and is 0.3 micrometer thick. It can clearly be seen from FIG. 3 that the combination of femoral head and hip-joint socket which is covered with a ceramic wear layer according to the invention exhibits the optimum wear behaviour.

Although the present invention has been described with reference to a hip prosthesis, the invention may also be used in other prostheses with parts which are movable with respect to one another, such as for example finger prostheses wrist prostheses, knee prostheses, and the like.

What is claimed is:

1. A joint prosthesis which comprises
   (1) a first metal member, and
   (2) a second metal member which is movable relative to the first member; the first and second members having wearing surfaces which rub against each other when the members are moved relative to each other, each of the wearing surfaces comprising
   (a) a base which is composed of (i) a metal matrix and (ii) metal carbide particles which are embedded in and project from the metal matrix, and
   (b) an abrasion layer which
      (i) covers the base,
      (ii) is less than 0.5 micrometer thick, and
      (iii) is composed of a ceramic material having a hardness which is greater than the hardness of the metal carbide particles.

2. A joint prosthesis according to claim 1, wherein the distance between the wearing surfaces is at most 0.4 mm.

3. A joint prosthesis according to claim 1, wherein the distance between the wearing surfaces is at most 0.2 mm.

4. A joint prosthesis according to claim 1, wherein the metal in the wearing surfaces of the first and second members is CrCoMo.

5. A joint prosthesis according to claim 1, wherein the ceramic material is TiNbON.

6. A joint prosthesis according to claim 1, which is a hip joint prosthesis wherein the first member is a socket member and the second member is a femoral head member.

7. A joint prosthesis according to claim 1, wherein the thickness of the abrasion layer is about 0.3 micrometer.

8. A joint prosthesis which comprises
   (1) a socket member, and
   (2) a head member which fits rotatably into the socket member; the socket and head members having wearing surfaces which rub against each other when the members rotate relative to each other, each of the wearing surfaces consisting essentially of
   (a) a base which is composed of (i) a metal matrix and (ii) metal carbide particles which are embedded in and project from the metal matrix, and
   (b) an abrasion layer which
      (i) covers the base,
      (ii) is less than 0.5 micrometer thick, and
      (iii) is composed of a ceramic material having a hardness which is greater than the hardness of the metal carbide particles.

9. A joint prosthesis according to claim 8, wherein the distance between the wearing surfaces is at most 0.4 mm.

10. A joint prosthesis according to claim 8, wherein the distance between the wearing surfaces is at most 0.2 mm.

11. A joint prosthesis according to claim 8, wherein the metal in the wearing surfaces of the first and second members is CrCoMo.

12. A joint prosthesis according to claim 11, wherein the ceramic material is TiNbON.

13. A hip joint prosthesis which comprises
   (1) a socket member, and
   (2) a femoral head member which has a diameter of at least 40 mm and fits rotatably into the socket member; the socket and head members (i) being separated from each other by distance of most 0.4 mm and (ii) having wearing surfaces which rub against each other when the members rotate relative to each other, each of the wearing surfaces consisting essentially of
   (a) a base which is composed of (i) a metal matrix and (ii) metal carbide particles which are embedded in and project from the metal matrix, and
   (b) an abrasion layer which
      (i) covers the base,
      (ii) is less than 0.5 micrometer thick, and
      (iii) is composed of a ceramic material having a hardness which is greater than the hardness of the metal carbide particles.

14. A joint prosthesis according to claim 13, wherein the distance between the wearing surfaces is at most 0.2 mm.

15. A joint prosthesis according to claim 13, wherein the socket member and the head member are composed of CrCoMo, and the ceramic material is TiNbON.

* * * * *